United States Patent
Lisowska et al.

(10) Patent No.: US 11,189,367 B2
(45) Date of Patent: Nov. 30, 2021

(54) SIMILARITY DETERMINING APPARATUS AND METHOD

(71) Applicant: CANON MEDICAL SYSTEMS CORPORATION, Otawara (JP)

(72) Inventors: Aneta Lisowska, Edinburgh (GB); Alison O'Neil, Edinburgh (GB); Ian Poole, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 212 days.

(21) Appl. No.: 16/368,913

(22) Filed: Mar. 29, 2019

(65) Prior Publication Data
US 2019/0371439 A1    Dec. 5, 2019

Related U.S. Application Data

(60) Provisional application No. 62/678,701, filed on May 31, 2018.

(51) Int. Cl.
*G16H 50/70* (2018.01)
*G16H 10/60* (2018.01)
(Continued)

(52) U.S. Cl.
CPC ............. *G16H 10/60* (2018.01); *G06N 20/00* (2019.01); *G16H 30/20* (2018.01)

(58) Field of Classification Search
CPC ... G06Q 50/22–24; G16H 10/60; G16H 30/20
See application file for complete search history.

(56) References Cited

U.S. PATENT DOCUMENTS

| | | | |
|---|---|---|---|
| 8,306,960 B2 * | 11/2012 | Kakimoto | G16H 50/20 707/705 |
| 2011/0046979 A1 * | 2/2011 | Tulipano | G16H 50/20 705/2 |

(Continued)

FOREIGN PATENT DOCUMENTS

| | | | |
|---|---|---|---|
| CN | 108595596 | * | 9/2018 |
| JP | 2001-142868 A | | 5/2001 |

(Continued)

OTHER PUBLICATIONS

CBMIR: Content-based Image Retrieval Algorithm for Medical Image Databases; Pilevar; 2011 (Year: 2011).*

(Continued)

*Primary Examiner* — John A Pauls
(74) *Attorney, Agent, or Firm* — Oblon, McClelland, Maier & Neustadt, L.L.P.

(57) ABSTRACT

An apparatus for determining similarity between medical data sets for a plurality of patients or other subjects comprises at least one data store and a processing resource. The at least one data store is configured to store a respective representation of each of a plurality of data sets, the representation of each data set being generated by applying a model for representing data sets with respect to a plurality of features. The processing resource is configured to use the model to obtain a representation of a further medical data set, and perform a similarity determining process to determine similarity between the representation of the further medical data set and at least some of said representations of said plurality of medical data sets.

19 Claims, 14 Drawing Sheets

(51) Int. Cl.
    *G06N 20/00*     (2019.01)
    *G16H 30/20*     (2018.01)

(56) References Cited

U.S. PATENT DOCUMENTS

| | | | |
|---|---|---|---|
| 2015/0170004 A1* | 6/2015 | Song | G06K 9/68 |
| | | | 382/218 |
| 2017/0053064 A1* | 2/2017 | Bhavani | G16H 40/63 |
| 2018/0293465 A1 | 10/2018 | Kanada | |
| 2019/0066847 A1* | 2/2019 | Jung | G16H 30/40 |

FOREIGN PATENT DOCUMENTS

| | | |
|---|---|---|
| JP | 2018-175226 A | 11/2018 |
| WO | WO 2018/116727 A1 | 6/2018 |

OTHER PUBLICATIONS

Xinran Liu, et al., "Generating Binary Tags for Fast Medical Image Retrieval Based on Convolutional Nets and Radon Transform" Proceedings of The 2016 IEEE International Joint Conference on Neural Networks (IJCNN 2016), Jul. 24-29, 2016, pp. 1-7.

Souvik Debnath, et al., "Feature Weighting in Content Based Recommendation System Using Social Network Analysis" Poster Paper, WWW 2008, Beijing, China, Apr. 21-25, 2008, pp. 1041-1042.

Amjad Almahairi, et al., "Augmented CycleGAN: Learning Many-to-Many Mappings from Unpaired Data" CoRR, http://arxiv.org/abs/1802.10151, 2018, 10 Pages.

Xiaosong Wang, et al., "ChestX-ray8: Hospital-Scale Chest X-Ray Database and Benchmarks on Weakly-Supervised Classification and Localization of Common Thorax Diseases" IEEE Xplore, CVPR 2017, 2017, pp. 2097-2106.

\* cited by examiner

Current Patient: 00002491_004 —112

—110

114 — {
Patient ID: 00002491_004
Age: 55
Gender: Male
View Position: PA
Finding: Atelectasis
}

Similar patients — 124

Filter by:

120

—130

122

126

—132

—134

—136

- Pathology A
- Pathology B

● Pathology A
▨ Pathology B

Age/yrs
1 — 90

SIMILARITY DETERMINING APPARATUS AND METHOD

FIELD

Embodiments described herein relate generally to a method and apparatus for determining similarity of data sets, for example medical data sets.

BACKGROUND

It is known to obtain and store medical images relating to patients or other subjects. Medical images can be produced using a wide range of imaging modalities for example, but not limited to, using computerized tomography (CT) scanners, X-ray modalities, ultrasound scanners, or positron emission tomography (PET) scanners.

The images that can be produced can take a variety of forms, and can include two-dimensional or three-dimensional representations for display on two-dimensional display screens. Medical images can be produced for a variety of purposes but are often used by medical practitioners for diagnostic or monitoring purposes and/or to assess particular medical conditions that may or may not be present.

Metadata concerning the medical images may also be stored. Metadata associated with a medical image may comprise, for example, information about the patient being imaged (for example age, gender, height or weight) and/or information about the anatomy to be imaged (for example, body part, orientation and pathology). Metadata associated with a medical image may comprise data (for example DICOM data) concerning the acquisition of the image. For example, the data concerning the image acquisition may comprise details of the scanner, modality and/or protocol used to acquire the image; an institution or geographical location where the image was acquired; and/or a date on which the image was acquired.

In some circumstances, medical images may be stored along with patient records comprising additional information about a patient and their medical history.

It is known to provide medical image retrieval systems which are configured to find medical images having certain characteristics. For example, a medical image retrieval system may be configured to find another patient that has a similar pathology to that of a patient of interest. Finding another patient that has a similar pathology to a pathology of a patient of interest may allow a clinician to compare images or other information for the similar patient to corresponding images or other information for the patient of interest. For example, the clinician may compare the treatment plan for the pathology or the progression of the pathology.

BRIEF DESCRIPTION OF THE DRAWINGS

Embodiments are now described, by way of non-limiting example, and are illustrated in the following figures, in which:

FIG. 9b is a schematic illustration of a similarity space corresponding to the importance values of FIG. 9a;

FIG. 10b is a schematic illustration of a similarity space corresponding to the importance values of FIG. 10a;

FIG. 11b is a schematic illustration of a similarity space corresponding to the importance values of FIG. 11a;

DETAILED DESCRIPTION

Figure 1:
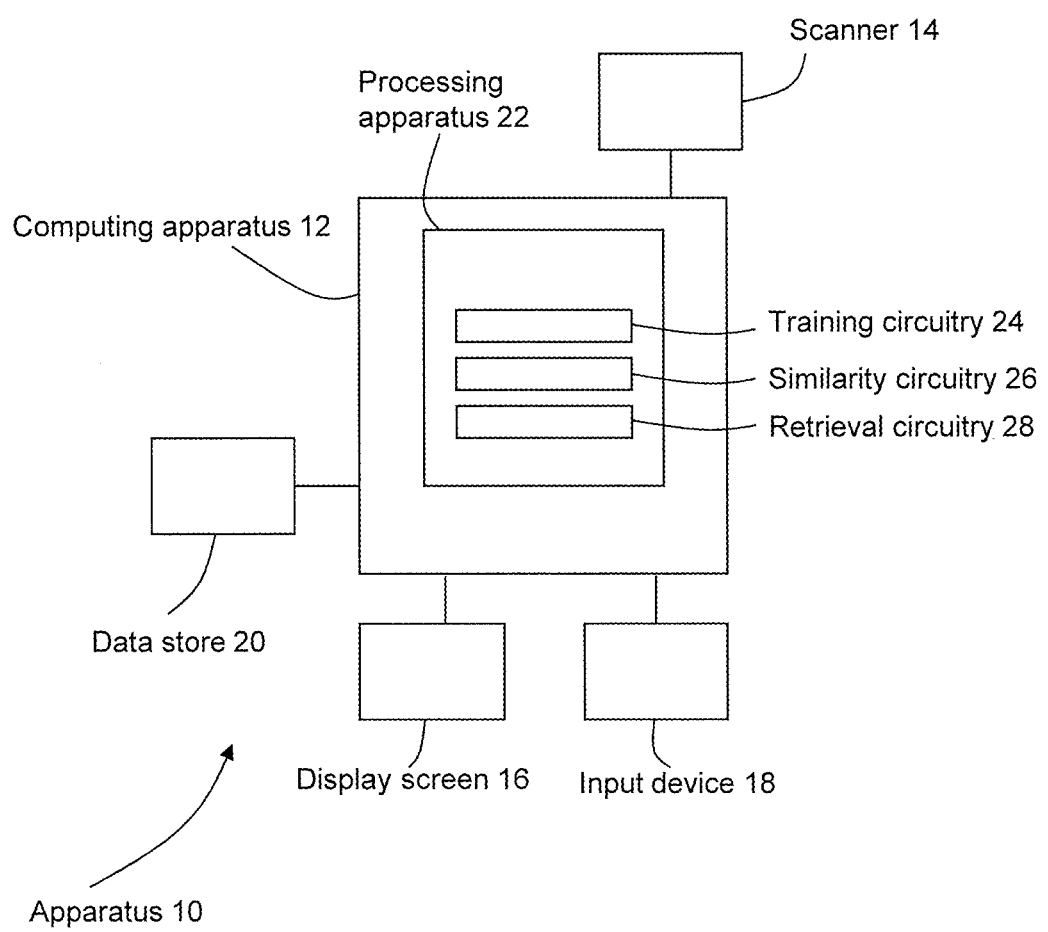
FIG. 1 is a schematic diagram of an apparatus according to an embodiment.

Certain embodiments provide an apparatus for determining similarity between medical data sets for a plurality of patients or other subjects, the apparatus comprising: at least one data store that stores, for a plurality of medical data sets, a respective representation of each of the plurality of medical data sets, the representation of each medical data set being generated by applying a model for representing data sets with respect to a plurality of features, the model being obtained by applying a machine learning process to a plurality of data sets to obtain the model based on classification and/or regression; and a processing resource that is configured to: use the model obtained by the machine learning process to obtain a representation of a further medical data set; perform a similarity determining process to determine similarity between the representation of the further medical data set and at least some of said representations of said plurality of medical data sets, wherein each of the representations comprises a set of data elements and for each representation at least some of the data elements have greater importance for determining similarity in respect of some attributes and have lesser importance for determining similarity in respect of some other attributes, and the processing resource is further configured to: select at least one attribute, or select an attribute weighting for at least one of the attributes, for use in the similarity determining process for the further data set; and for at least some of the medical data set representations, selectively apply different weightings to at least some of data elements of the representation for use in the similarity determining process, depending on attributes or attribute weightings that have been selected, and on the relative importance of the different data elements for the selected attributes or attribute weightings.

Certain embodiments provide a method of determining similarity between medical data sets for a plurality of patients or other subjects, the method comprising: storing for a plurality of medical data sets a respective representation of each of the plurality of medical data sets, the representation of each medical data set being generated by applying a model for representing data sets with respect to a plurality of features, the model being obtained by applying a machine learning process to a plurality of data sets to obtain the model based on classification and/or; using the model obtained by the machine learning process to obtain a representation of a further medical data set; performing a similarity determining process to determine similarity between the representation of the further medical data set and at least some of said representations of said plurality of medical data sets, wherein each of the representations comprises a set of data elements and for each representation at least some of the data elements have greater importance for determining similarity in respect of some attributes and have lesser importance for determining similarity in respect of some other attributes, and the method further comprises: selecting at least one attribute, or selecting an attribute weighting for at least one of the attributes, for use in the similarity determining process for the further data set; and for at least some of the medical data set representations, selectively applying different weightings to at least some of data elements of the representation for use in the similarity determining process, depending on attributes or attribute weightings that have been selected, and on the relative importance of the different data elements for the selected attributes or attribute weightings.

Certain embodiments provide a computer program product comprising computer-readable instructions that are executable to: store for a plurality of medical data sets a respective representation of each of the plurality of medical data sets, the representation of each medical data set being generated by applying a model for representing data sets with respect to a plurality of features, the model being obtained by applying a machine learning process to a plurality of data sets to obtain the model based on classification and/or; use the model obtained by the machine learning process to obtain a representation of a further medical data set; perform a similarity determining process to determine similarity between the representation of the further medical data set and at least some of said representations of said plurality of medical data sets, wherein each of the representations comprises a set of data elements and for each representation at least some of the data elements have greater importance for determining similarity in respect of some attributes and have lesser importance for determining similarity in respect of some other attributes, and the computer-readable instructions are further executable to: select at least one attribute, or select an attribute weighting for at least one of the attributes, for use in the similarity determining process for the further data set; and for at least some of the medical data set representations, selectively apply different weightings to at least some of data elements of the representation for use in the similarity determining process, depending on attributes or attribute weightings that have been selected, and on the relative importance of the different data elements for the selected attributes or attribute weightings.

An apparatus 10 according to an embodiment is illustrated schematically in FIG. 1. In the embodiment of FIG. 1, the apparatus 10 is configured to train a classifier to identify features associated with different similarity dimensions, and to use the trained classifier to retrieve similar images. In other embodiments, a first apparatus may be used to train the classifier and a second, different apparatus may use the trained classifier to retrieve similar images. In further embodiments, any apparatus or combinations of apparatuses may be used.

The apparatus 10 comprises a computing apparatus 12, in this case a personal computer (PC) or workstation, which is connected to a scanner 14, one or more display screens 16 and an input device or devices 18, such as a computer keyboard, mouse or trackball.

The scanner 14 may be any scanner that is configured to perform medical imaging. The scanner 14 is configured to generate image data that is representative of at least one anatomical region of a patient or other subject. The scanner may be configured to obtain two-dimensional or three-dimensional image data in any imaging modality. For example, the scanner 14 may comprise a magnetic resonance (MR or MRI) scanner, CT (computed tomography) scanner, cone-beam CT scanner, X-ray scanner, ultrasound scanner, PET (positron emission tomography) scanner or SPECT (single photon emission computed tomography) scanner. In further embodiments, the scanner may generate any type of image data, which may not be medical image data. In other embodiments, the computing apparatus 12 may not be connected to a scanner or scanners 14.

In the present embodiment, image data sets obtained by the scanner 14 are stored in data store 20 and subsequently provided to computing apparatus 12. The image data sets form part of medical data sets that are stored in data store 20. Each medical data sets may comprise at least one image data set, and may further comprise additional information about the scan that produced the image data set and/or about the patient or other subject of the image data set.

In an alternative embodiment, image data sets and/or medical data sets are supplied from a remote data store (not shown) which may form part of a Picture Archiving and Communication System (PACS). The data store 20 or remote data store may comprise any suitable form of memory storage.

Computing apparatus 12 comprises a processing apparatus 22 for processing of data, including image data. The processing apparatus comprises a central processing unit (CPU) and Graphical Processing Unit (GPU).

The processing apparatus 22 provides a processing resource for automatically or semi-automatically processing data sets. In the present embodiment, the data sets comprise medical image data. For simplicity, we will refer below to the processing and retrieval of medical images. However, operations described below as being performed on medical images may in practice be performed on any suitable sets of image data that are representative of medical images. Image data may be processed internally by the processing apparatus 22 without any corresponding image being displayed.

The processing apparatus 22 includes training circuitry 24 configured to train a classifier to identify features associated with similarity dimensions, similarity circuitry 26 configured to determine similarity between data sets, and retrieval circuitry 28 configured to retrieve similar images.

In the present embodiment, the circuitries 24, 26, 28 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
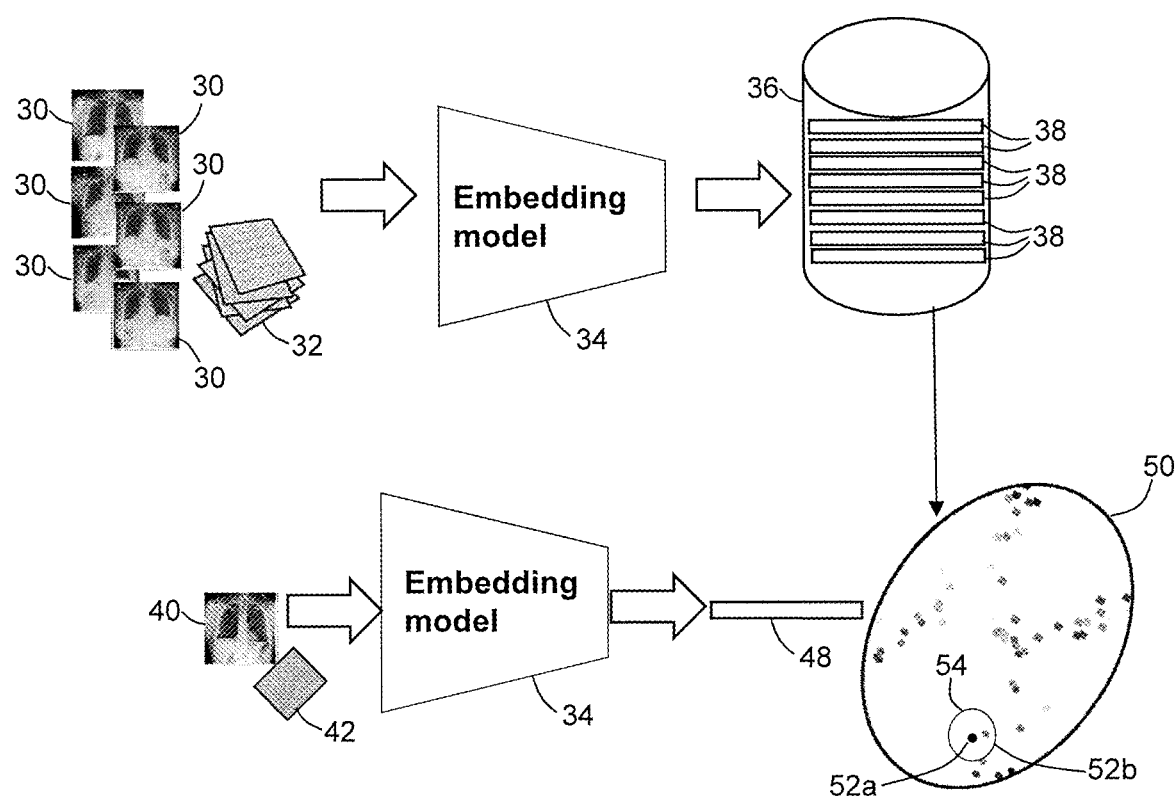
FIG. 2 is a flow chart illustrating in overview a method of determining similarity of medical data sets.

FIG. 2 is a flow chart illustrating in overview a method of determining similarity of medical data sets. The method of FIG. 2 may be considered to provide a standard set up for medical image retrieval.

During installation of a medical image retrieval apparatus, the medical image retrieval apparatus receives a plurality of medical images 30 obtained from patient imaging, and medical records 32 associated with the patients for whom imaging was performed.

The medical images 30 and medical records 32 form a plurality of medical data sets, each data set comprising at least one medical image and associated medical record data. Each data set may comprise metadata concerning the patient, anatomy and/or acquisition.

The medical data sets are processed using an embedding model 34. The embedding model 34 outputs a compressed representation database 36. The compressed representation database 36 comprises, for each medical data set, a respective fixed-length one-dimensional vector 38 that may be considered to be a compressed representation of the medical data set. The one-dimensional vector 38 is compressed in comparison to the medical data set. The one-dimensional vector 38 is of reduced dimension in comparison to the medical data set.

The one-dimensional vectors 38 for each of the medical data sets are projected into a similarity space. Each one-dimensional vector 38 is represented by a point in the similarity space. Each vector 38 is a representation of a data point having dimensionality n. The choice of n is a design choice which may be made based on how rich the representation needs to be to capture information about the similarity dimensions for the population distribution.

In the example of FIG. 2, the similarity space may be considered to be a default similarity space. When the patient cohort is projected to the default similarity space, the points representing each medical data set in the patient cohort have fixed positions in the default similarity space. The positions of the points do not change in dependence on which queries are made of the system.

In FIG. 2, the similarity space is represented by space 50, which shows a two-dimensional projection of the similarity space. For visualization purposes, when we have multiple vectors we can project them into a lower dimensional space using dimensionality reduction methods such as multidimensional scaling (MDS), which preserves the distance between the data points in the high dimensional space.

A plurality of points 52 are positioned in space 50. Each point is representative of the one-dimensional vector 38 that has been obtained for a respective medical data set. If two points 52 are close to each other in space 50, the medical data sets represented by those points considered to be similar. If two points 52 are far from each other in space 50, the medical data sets represented by those points are considered to be dissimilar.

In the method of FIG. 2, a single set of criteria for similarity is used. The method of FIG. 2 can only be used to determine one fixed type of similarity.

In use time, the medical image retrieval apparatus receives a further medical data set for a current patient under review. The further medical data set comprises current patient imaging 40 comprising at least one further medical image. The further medical data set further comprises records 42 comprising further information about the patient and/or image(s).

The medical image retrieval apparatus applies the embedding model 34 to the further medical data set to obtain a compressed representation 48 of the further medical data set. The compressed representation 48 comprises a fixed-length one-dimensional vector. The compressed representation 48 may be considered to be a default compressed representation. The compressed representation would be obtained in the same way for any image retrieval request and any current patient.

Turning again to space 50, point 52a is representative of the further medical data set for the current patient under review. A distance from point 52a is representative of a degree of similarity to the further medical data set. A circle 54 drawn around point 52a may be considered to be representative of a contour of constant similarity. The only other point within the circle 54 is point 52b. The medical data set represented by point 52b may therefore be considered to be the medical data set that is most similar to the further medical data set. The medical data set represented by point 52b may be referred to as the most similar medical data set or the default most similar patient case.

Once the most similar medical data set has been determined, the medical image retrieval apparatus retrieves at least part of the most similar medical data set. For example, the medical image retrieval apparatus may retrieve at least one image of the medical data set. The at least one image may be displayed to a user, for example to a clinician.

In the example shown in FIG. 2, the way that similarity is defined is fixed. Similarity between medical data sets is always determined based on the difference between the fixed-length 1D vectors produced by the embedding model.

The method of FIG. 2 does not take into account different types of similarity. For example, the method of FIG. 2 may only output images that are similar in pathology and may not take into account other aspects of similarity such as patient age and gender.

In some circumstances, it may be difficult to foresee which dimensions (aspects) of patient similarity may be of interest to the user for a given clinical scenario.

Frequently medical image retrieval systems are focused only on finding patients with similar presenting pathology. Such systems may neglect similarity in terms of other qualities, for example age, gender, anatomy, ethnicity, coexisting conditions, point in the treatment pathway (time since onset, treatments applied, time since treatment, etc.).

If the hospital database has metainformation about the patient, it may be possible to filter patients explicitly by using metadata. For example, the medical data sets may be filtered to only consider medical data sets for patients having the same gender when determining similarity.

However, in general filtering by metadata will not incorporate visual similarity of two scans. Filtering by metadata may not provide a ranked list if the filter is binary (for example a binary filter for whether the patient is male or female). Further, some of the metainformation may not be available in all cases at deployment.

In an embodiment, a machine learning process is used to obtain a respective representation of each of a plurality of medical data sets. The representation that is obtained by the machine learning process may be used, with appropriate weightings, to take into account different types of similarity. A clinician may select which dimension or dimensions of similarity are important for the current patient case under review.

Figure 3:
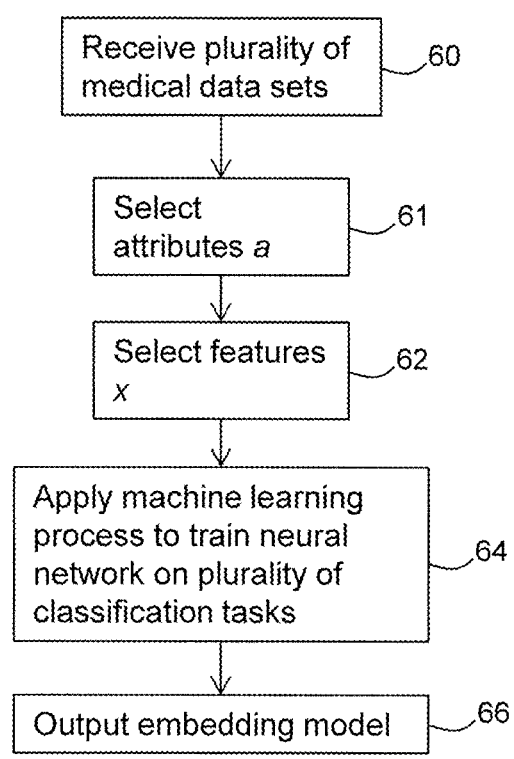
FIG. 3 is a flow chart illustrating in overview a machine learning process in accordance with an embodiment.

FIG. 3 is a flow chart illustrating in overview a machine learning process in which a classifier is trained using a plurality of medical data sets. In the present embodiment, the machine learning process comprises a convolutional neural network (CNN) process in which a convolutional neural network is trained. In other embodiments, the machine learning process may comprise any suitable classifier training process.

At stage 60, the training circuitry 24 receives a plurality of medical data sets. Each medical data set comprises data representing at least one property of a patient or other subject of the data set in question. Each medical data set comprises at least one medical image and associated medical record data. Each data set may comprise metadata concerning the patient, anatomy and/or acquisition. The medical images may comprise CT images, MR images, X-ray images, fluoroscopy images, PET images, or any other suitable medical images.

At stage 61, the training circuitry 24 selects a number m of attributes a. The attributes a may be selected, for example, based on a predetermined list or based on user input.

The attributes a are representative of dimensions of similarity (which may also be described as aspects of similarity). The attributes selected at stage 60 are attributes a for which a user will be allowed to select weights in accordance with an importance of the attributes.

In the present embodiment, the selected attributes a are gender, age and pathology. In a further embodiment, the selected attributes a additionally include scan view, anatomy and at least one other attribute. In other embodiments, the selected attributes a may include at least one of age; gender; presence, absence or nature of pathology; presence or absence of anatomical feature; ethnicity; coexisting condition; point in treatment pathway; time since onset; treatment applied; time since treatment; or any other suitable attribute. The attributes may comprise at least one image attribute and at least one non-image attribute.

Before training, each attribute is normalized such that a value for each attribute is expressed as a number between 0 and 1. For example, values for age may be normalized such that a normalized age of 0 is representative of a chronological age of 0 and a normalized age of 1 is representative of a chronological age of 90 or over.

At stage 62, the training circuitry 24 selects a plurality p of features x to be used in a machine learning process. The features x are parameters that may be expected to be obtained from the medical data sets. The features x may be selected, for example, based on a predetermined list or based on user input.

The features may include at least one of age; gender; presence, absence or nature of pathology; presence or absence of anatomical feature; ethnicity; coexisting condition; point in treatment pathway; time since onset; treatment applied; time since treatment;

or any other suitable feature.

The features may include image parameters of a medical image, for example maximum intensity, intensity range, intensity gradient, texture feature. The features may include information from medical image metadata, for example, scanner, modality, protocol, date, institution, geographical location, or date. The features may include information from medical records, for example, test results, measurements, scores, or diagnosis. The features may include free-text information, for example from radiology reports, referral letters, or discharge summaries The features may include demographic information, for example age or gender. The features may include at least one image feature and at least one non-image feature.

In the present embodiment, the medical data sets already comprise values for each of the selected features. In some embodiments, the training circuitry 24 may process at least some of the medical data sets to obtain values for at least some of the selected features.

Some variables may be either features or attributes depending on the system. For example, age may be used as a feature in some embodiments, and may be used as an attribute in another system. For example, a patient scan may be used as an input from which to predict the age of the patient (an attribute). It may then be possible to look at the model weights and identify which features extracted from the original input (in this case, the patient scan) were important for the task of predicting this attribute.

Each feature x is normalized such that a value for each feature x is expressed as a number between 0 and 1.

At stage 66, the training circuitry 24 performs a machine learning process in which the convolutional neural network learns how to determine similarity for each of the attributes a based at least partially on the features x. The training circuitry 24 is trained on a plurality of medical data sets, which may be referred to as a training set or training cohort.

The training set may be a rich training data set in which ground truth values are available for multiple attributes of each patient. For example, a medical data set used for training may comprise a patient scan and/or a discharge letter. Ground truth values may be provided for attributes of the medical data set including, for example, gender, age, ICD (International Classification of Diseases) code, suggested treatment. If the medical data set comprises an image, other possible attributes may include anatomy segmentation or pathology marking.

The neural network is trained on multiple classification tasks. For example, the neural network may be trained to perform a first classification task comprising classifying medical data sets by age. The neural network may be trained to perform a second classification task comprising classifying medical data sets by gender. The neural network may be trained to perform a third classification task comprising classifying medical data sets by pathology. In embodiments, the machine learning process may comprise any suitable classification and/or regression tasks.

In the classification training process, the neural network learns which of the features x are relevant to each classification task. The classifier training process comprises the performance of similarity determination tasks with respect to the plurality of features x. It may be expected that different features x are relevant to different classification tasks.

In the present embodiment, the neural network also learns at least one further feature y, which may be described as an emergent feature. An emergent feature y is a feature that is found in training to be relevant to at least one classification (or regression) task, but is not included in the features x that were initially selected at stage 62.

If we train a classifier on multiple classification tasks, then it will implicitly contain information about similarity in each dimension (or task) for which it was trained.

In the present embodiment, the machine learning process comprises generating a succession of layers, each layer comprising a set of data elements. Each layer is based upon the preceding layer or layers.

At stage 66, the machine learning process outputs a model 70, which may be described as an embedding model.

The embedding model is configured to receive medical data and to output, for each data set, a one-dimensional vector s. s may be described as an embedding vector. s is a one-dimensional vector of size n.

The embedding vector s corresponds to a final layer of the succession of layers generated by the machine learning process. The final layer can be used to determine similarity with respect to the features x and any emergent features y that are not explicitly included in the plurality p of features x that were originally selected.

The embedding vector s comprises n data elements. In the present embodiment, the n data elements of the embedding vector comprise the plurality p of features x that were initially selected, plus a further emergent feature y. In other embodiments, the data elements may comprise any suitable number of features and/or emergent features.

Figure 4:
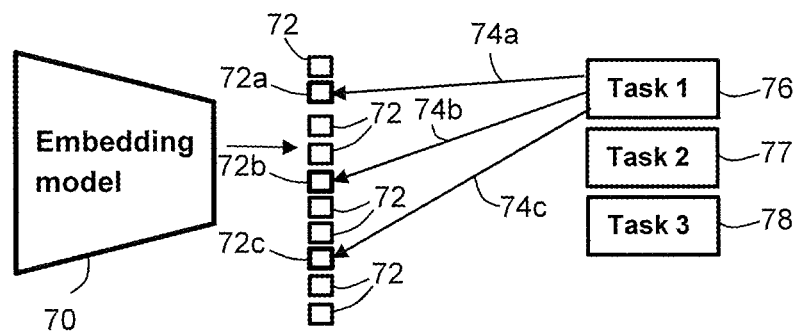
FIG. 4 is an illustration of training an embedding model to perform classification tasks.

FIG. 4 is representative of a process of generating an embedding model 70 using a plurality of classification tasks 76, 77, 78. A particular example of a classification task 76 is shown as Task 1 in FIG. 4. In the machine learning process, it is found that out of a set of data elements 72, three of the data elements 72a, 72b, 72c are relevant to the first classification task 76. The relationship between the first classification task 76 and the data elements 72a, 72b, 72c is shown by arrows 74a, 74b, 74c. Although not shown in FIG. 4, different ones of the data elements 72 are relevant to a second classification task 77 (Task 2) and a third classification task 78 (Task 3).

The machine learning process further outputs a respective weighting vector $w_a$ for each of the attributes a. The weighting vector $w_a$ is a one-dimensional vector of size n. The weighting vector $w_a$ comprises a set of learned weights for the attribute a.

Figure 5:
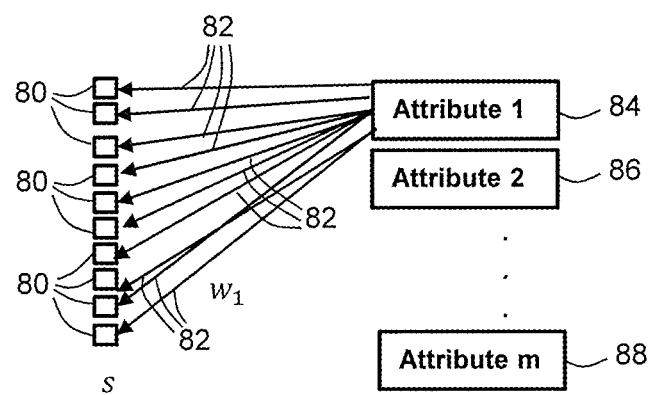
FIG. 5 is an illustration of a weighting vector for an attribute in relation to an embedding vector.

FIG. 5 shows an embedding vectors comprising a plurality of data elements 80. The weighting vector $w_1$ associated with a first attribute 84 is represented by a plurality of arrows 82, each representing a respective one of the learned weights in the weighting vector $w_1$. Different weighting vectors $w_a$ will be associated with further attributes from second attribute 86 up to mth attribute 88.

Figure 6:
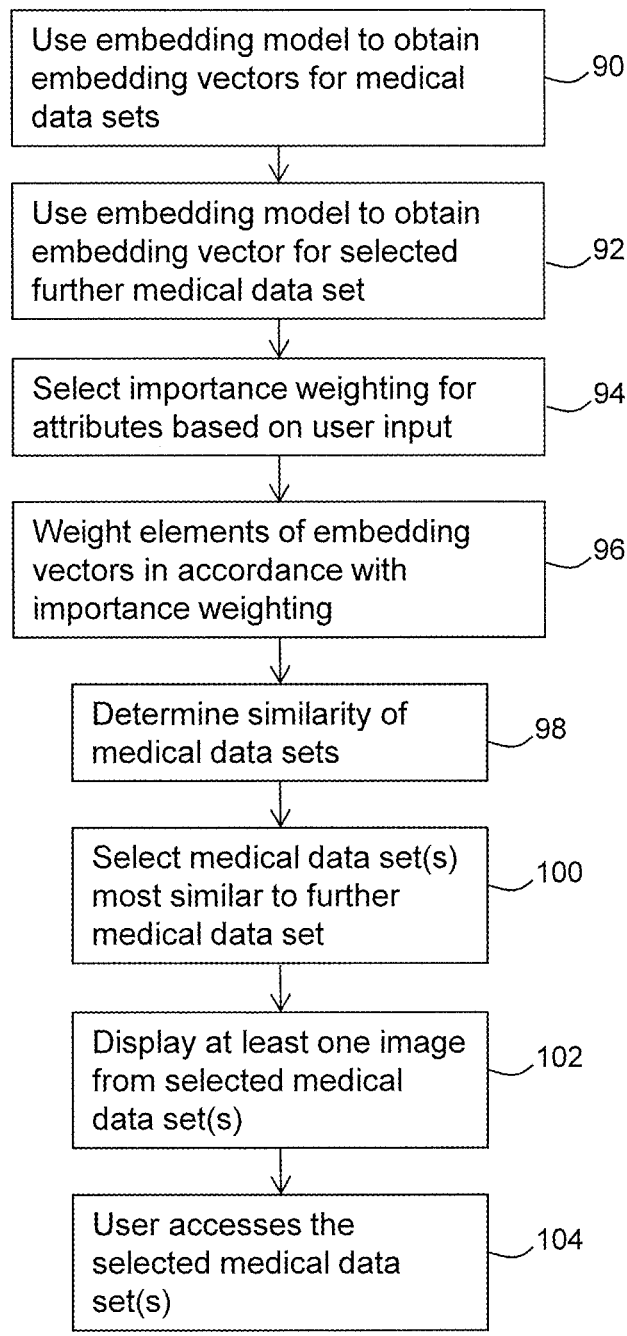
FIG. 6 is a flow chart illustrating in overview a method for using an embedding model to determine similarity.

FIG. 6 is a flow chart illustrating in overview a method for using an embedding model to determine similarity. In the embodiment of FIG. 6, the embedding model and associated weighting vectors $w_a$ for attributes a have been obtained using a machine learning process, for example a machine learning process as described above with reference to FIG. 3.

At stage 90 of FIG. 6, the similarity circuitry 26 uses the embedding model to obtain a respective embedding vector s for each of a plurality of stored medical data sets. In some embodiments, at least some of the medical data sets are medical data sets on which the machine learning process was performed.

In other embodiments, the stored medical data sets are different from the data sets on which the model was trained. In some embodiments, training data sets, validation data sets and/or test data sets may be used for developing the system. For example, a set of training data sets may be used to train the embedding model, validation data sets may be used to validate the embedding model, and test data sets may be used to test the embedding model.

In many embodiments, the stored medical data sets used at stage 90, which are used at deployment to select similar different data sets, are different from the data sets on which the model was trained. The stored medical data sets that are used at deployment may come from an institution in which the system is deployed, which may allow a doctor using the system to access the full history of any similar patients for a given case of interest.

In the present embodiment, the medical data sets comprise medical images that were obtained by scanner 14 and stored in data store 20. In other embodiments, the medical data sets may comprise any suitable data types, which may or may not include images. The medical data sets may be stored in any suitable data store in any suitable data format.

For each medical data set, the embedding vector s provides a compressed representation of the medical data set. The embedding vector s is of reduced dimension in comparison to the medical data set. The embedding vectors s are stored in the data store 20. In other embodiments, the embedding vectors s may be stored in any suitable data store 20

At stage 92, the similarity circuitry 26 receives a further medical data set. The further medical data set is selected by a user, for example a clinician. In some circumstances, the further medical data set may comprise at least one medical image that has been recently acquired by the scanner 14. The further medical data set may relate to a patient or other subject of interest.

The similarity circuitry 26 uses the embedding model to obtain an embedding vector s for the further medical data set.

At stage 94, the similarity circuitry 26 selects an importance weighting for each of a plurality of attributes a. The plurality of attributes a includes at least some of the attributes for which the machine learning process was performed to obtain the embedding model.

The similarity circuitry 26 selects the importance weighting for each of the plurality of attributes a based on a user input.

A user (for example, a clinician) selects a respective importance value $f_a$ for each of the attributes a. The importance value may also be referred to as an importance weighting. The importance value $f_a$ for each attribute a is a value between 0 and 1. A value of 0 means that we do not want to consider the attribute.

In other embodiments, the importance value $f_a$ for each attribute a is between −1 and 1. Therefore, both positive and negative weightings can be applied. Negative attributes may be relevant when more than one feature is considered and may reflect negative correlation between features. The system may be invariant to negation of all feature weights.

The selection of a high value of importance $f_a$ by a user for a given attribute indicates that the user wants to find medical data sets that are similar in terms of that attribute. For example, if the user sets a high importance $f_a$ for age, the user wishes to find medical data sets having similar age to that of the patient of interest.

In further embodiments, the user may select at least one of the attributes. The user may select at least one of the attributes without explicitly providing importance values. For example, the importance value $f_a$ for each selected attribute may be automatically set to 1.

The user may select the at least one attribute, or the importance weighting for at least one attribute, based on a clinical scenario relevant to the further data set, a type of image data included in the further data set, an imaging modality, results of at least one test or procedure performed on the patient or other subject of the further data set, or for any suitable reason.

The user selects the importance values via a user interface. The user may select the importance weightings in any suitable manner. The user may input the importance weightings using any suitable input device or devices 18. The user may input the importance weighting using a slider, a button, a list of values, a list of attributes, or any at least one selectable element.

In other embodiments, the similarity circuitry 26 selects at least one of the attributes, or the attribute weighting, based on the user input.

In the present embodiment, $f_0$ is an importance weighting for an attribute arising from emergent behavior. In the present embodiment, $f_0$ is not set by the user. $f_0$ is set to a small default value, for example 0.2.

For a in {1:m}, $f_a$ is an importance of the attribute a, obtained from the user.

At stage 96, the similarity circuitry 26 weights elements of each of the embedding vectors in accordance with the importance weighting provided at stage 94.

s' is a modified version of s, which is modified in accordance with the importance indicated by the user. s' is calculated as shown below:

$$s' = \frac{1}{z}\sum_{a=0}^{m} f_a(s * w_a)$$

where * indicates elementwise multiplication, $f_0$ is the importance weighting for the emergent attribute (which is not provided by the user), $f_1$ to $f_m$ are the user-provided importance weightings for the m attributes, and $w_a$ are the weighting vectors for the attributes which are normalized and take absolute values as shown below.

$$w_a = \frac{|w_a|}{\|w_a\|}$$

z provides normalisation. z is calculated as shown below:

$$z = \sum_{a=0}^{m} |f_a|$$

Setting $f_0$ to a small default value may prevent a case occurring in which z=0.

In stage 96, the importance weightings $f_0$, $f_a$ and the weighting vectors $w_a$ are applied without altering the machine learning process that was performed using the method of FIG. 3. The importance weightings $f_0$, $f_a$ and the weighting vectors $w_a$ are applied without altering any inputs to the machine learning process of FIG. 3. The embedding model and weighting vectors $w_a$ that were generated in the process of FIG. 3 allow for a relative importance of different attributes to be changed at will, without changing the embedding model or weighting vectors.

At stage 98, the similarity circuitry 26 performs a similarity determining process. In the similarity determining process, the similarity circuitry 26 determines the similarity of at least some of the medical data sets to the further medical data set by calculating a distance from the modified embedding vector s' for the further medical data set to each of the modified embedding vectors s' for the medical data sets.

In the present embodiment, the distance between modified embedding vectors is calculated using cosine similarity. In other embodiments, any suitable method of calculating a distance between the modified embedding vectors may be used.

At stage 100, the retrieval circuitry 28 selects the medical data set that is most similar to the further medical data set as determined based on the modified embedding vectors s'.

In further embodiments, the retrieval circuitry 28 selects a plurality of most similar medical data sets. For example, the retrieval circuitry 28 may select the 5, 10 or 20 medical data sets that are considered to be most similar to the further medical data set based on the modified embedding vectors s'. The retrieval circuitry 28 may rank the selected medical data sets in order of similarity.

At stage 102, the retrieval circuitry 28 outputs at least part of the selected medical data set or sets. In the present embodiment, the outputting comprises displaying at least one medical image from the selected most similar medical data set on the display 16. In other embodiments, the at least one medical image may be displayed on any suitable display. In further embodiments, any suitable data from the medical data set may be displayed to the user on the display screen 16 or on an additional or alternative display screen.

In further embodiments, the retrieval circuitry 28 outputs an identifier that identifies the selected medical image set or sets.

At stage 104, the user may access the selected medical data set or sets. In the present embodiment, the user views the displayed medical image and may view further medical images that are part of the same medical data set or of an associated medical data set. The user may also view medical records pertaining to the patient or other subject of the medical data set.

In some embodiments, a plurality of most similar medical data sets are selected, and a part of each selected medical data sets is displayed to the viewer. In one embodiment, for each selected medical data set a medical image is displayed along with patient age and gender. In other embodiments, details of other attributes may be provided. The patient can choose one of more of the selected medical data sets to view, for example by clicking on one of the medical images or by any other suitable input method.

By using the method of FIG. 6 and the model and weighting vectors generated using the method of FIG. 3, a user (for example, a clinician) may select which dimension or dimensions of similarity are important to the user. The user may select which dimension or dimensions of similarity are important for a current patient case under review. The associated features are then given a high weighting in the similarity matching.

The user is enabled to have fine control by specifying the importance of each similarity dimension as a continuous value between 0 and 1. This is then reflected in the feature weighting. Weighting vectors to implement the user-specified importance are determined at training time, from the final layer of the neural network.

Different dimensions of similarity may be important in different clinical scenarios. The same attributes could be less important in a given clinical scenario. Other attributes could be more important for a patient case under review. For example, age may be important to similarity for some pathologies while being less important to others. Gender may be important to similarity for some pathologies while being less important to others.

The features associated with each similarity dimension are identified in the embedding vector and weighted according to the importance specified by the clinician. A most similar patient case is identified, where the most similar patient case reflects the importance in each similarity dimension.

The use of a compressed representation of the medical data sets may allow similar sets to be accessed rapidly during use.

The ability to weight the importance of each similarity dimension may result in more useful similar patient suggestions for a current patient case. Control of dimensions of similarity may be provided to the user. Providing the user with control of similarity may be beneficial as it may not be possible to predict in advance which dimensions of similarity are likely to be important to the user in every clinical scenario.

The machine learning process may produce an embedding that represents any requested dimensions of similarity. The machine learning process may identify emergent features that have not been supplied to the machine learning process as an input.

Visual similarity of medical images may be taken into account, for example by using attributes and/or features that are representative of visual similarities between images.

The method of FIG. 6 may output a ranked list that takes into account multiple dimensions of similarity. For example, instead of filtering the stored medical data sets by gender, gender may be just one factor in similarity. In some circumstances, medical data sets that are a good match for pathology and are of the requested gender may be ranked above data sets that are a good match for pathology and are of another gender. However, medical data sets that are a good match for pathology and of a gender other than the requested gender may be ranked above medical data sets that are of the preferred gender but are a poorer match for pathology.

The user may adjust the importance settings if they do not receive results that they expected.

In some embodiments, the similarity circuitry 26 may store a preset importance values associated with particular clinical scenarios. The user may select which preset importance values to use by selecting a clinical scenario.

Figure 7:
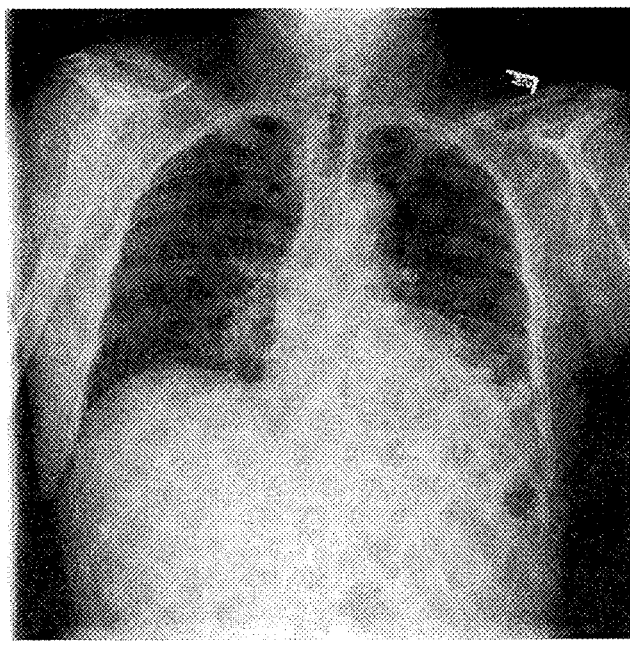
FIG. 7 is a schematic illustration of a user interface.
Figure 7:
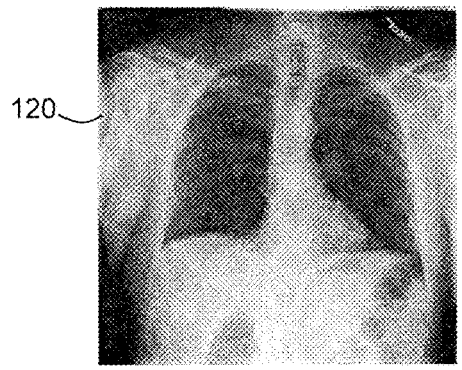
Figure 7:
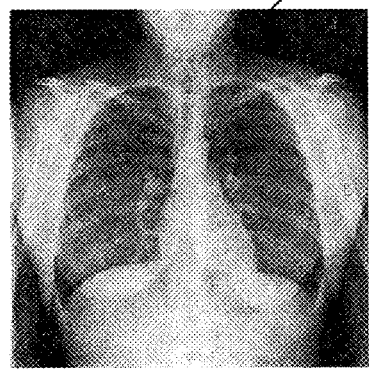
Figure 7:
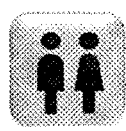
Figure 7:
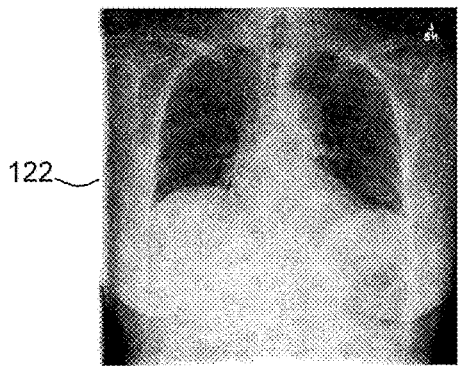
Figure 7:
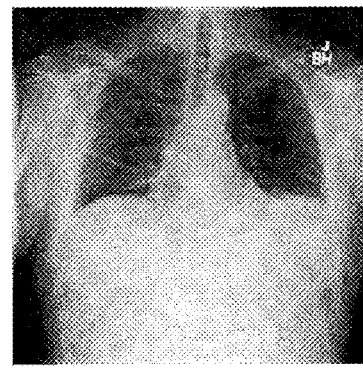
Figure 7:
Figure 7:
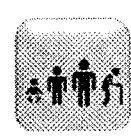
Figure 7:
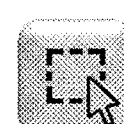

FIG. 7 is a schematic illustration of a user interface in accordance with an embodiment.

An image 110 of a current patient is displayed on the user interface, which may be displayed on display screen 16 or on an alternative or additional display. A patient ID 112 is also shown on the user interface, along with some patient information 114. In the present embodiment, the patient information comprises patient age, gender, view position and finding.

The user interface further displays images 120, 122, 124, 126 of similar patients. Similarity may be determined in any suitable method, for example by using the method of FIG. 2 or the method of FIG. 6.

A set of buttons 130, 132, 134, 136 are also presented on the user interface, each having a respective icon. The icon on button 130 is representative of gender. The icon on button 132 is representative of scan view. The icon on button 134 is representative of age. The icon on button 136 is representative of a selection of a specific anatomical region of interest within the image. A dashed rectangular box within the icon of button 136 is derived from a representation of a rectangular selection tool used to select a region of interest.

By clicking one or more of the buttons 130, 132, 134, 136, the user may filter the similar patients by gender, scan view, age or region of interest respectively.

Figure 8:
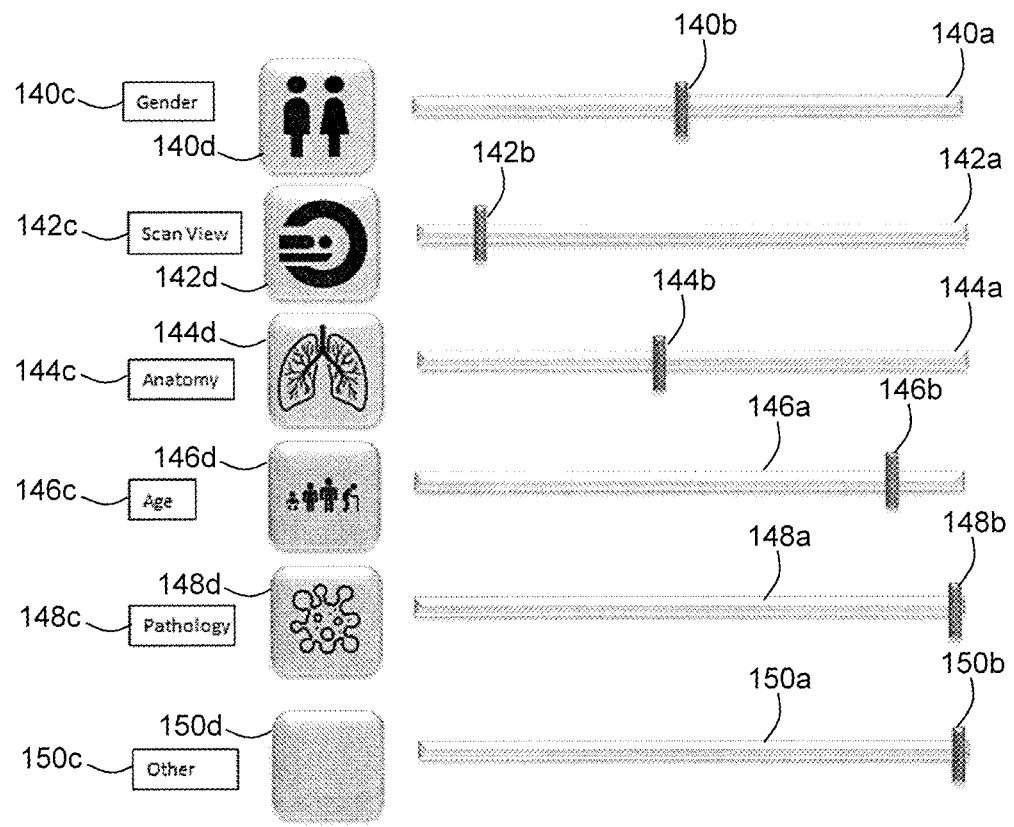
FIG. 8 is a schematic illustration of an example of a user interface for specifying feature importance in accordance with an embodiment.
Figure 8:
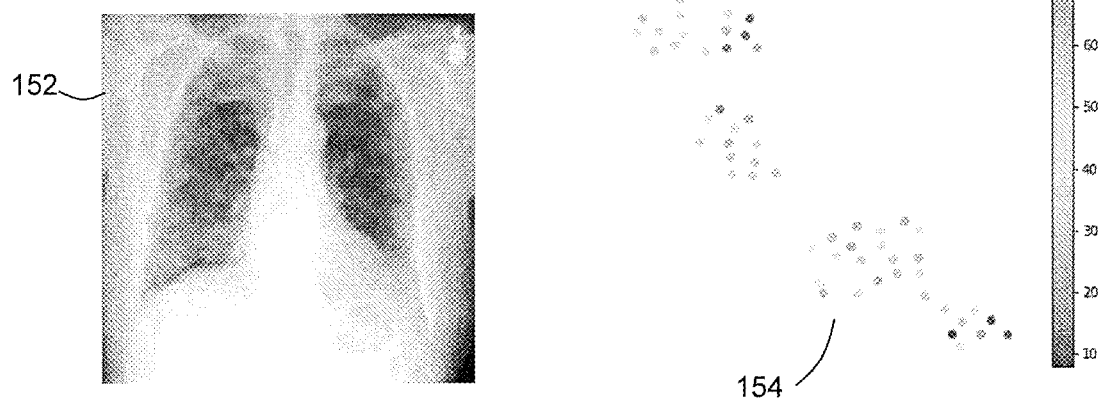

FIG. 8 is a schematic illustration of an example of a user interface for specifying importance of each attribute in accordance with an embodiment.

The user interface comprises six of slider bars 140a, 142a, 144a, 146a, 148a, 150a. Each slider bar 140a, 142a, 144a, 146a, 148a, 150a comprises a slider control 140b, 142b, 144b, 146b, 148b, 150b which is controllable by a user to select a position on the slider bar and thereby to select a value for importance between −1 and 1.

Each slider bar 140a, 142a, 144a, 146a, 148a, 150a is shown with a corresponding label 140c, 142c, 144c, 146c, 148c, 150c and icon 140d, 142d, 144d, 146c, 148d, 150d. In the embodiment shown in FIG. 8, the labels and icons represent gender, scan view, anatomy, age, pathology and other respectively. The slider bar 150a which is labelled other may be used, for example, to control importance of an emergent attribute that has been identified in training.

The user interface further comprises a medical image 152 for a current patient of interest. The user interface further comprises a plot 154 which is representative of a similarity space. Points on the plot 154 are representative of medical data sets. The scale of the plot 154 is representative of age in years from young to old. In many embodiments, the plot 154 is not included in the user interface.

Figure 9A:
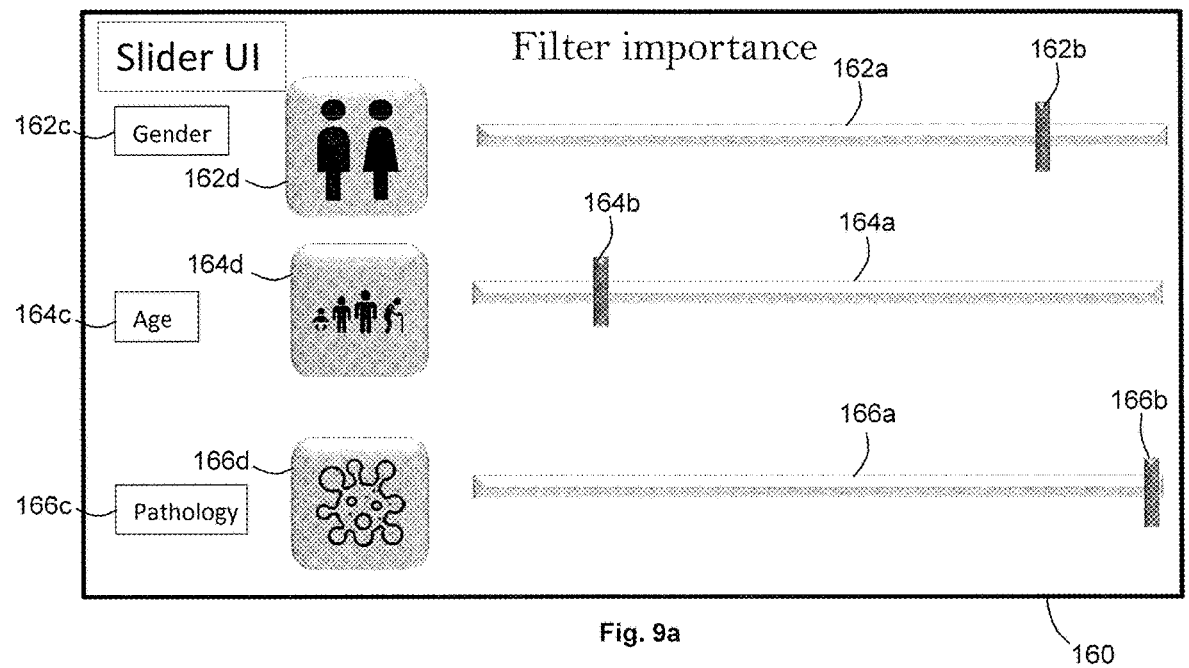
FIG. 9a is a schematic illustration of a user interface in accordance with an embodiment, in which slider bars are used to select importance values.

FIG. 9a is a schematic illustration of a user interface 160 in accordance with an embodiment. The user interface may be referred to as a slider user interface or slider UI.

The slider UI comprises three slider bars 162a, 164a, 166a, each of which has a respective slider control 162b, 164b, 166b which is moveable by a user.

A first slider bar 162a is associated with gender. In the present embodiment, a first text description 162c and a first icon 162d are both used to indicate that the first slider bar is representative of gender.

A second slider bar 164a is associated with age. A second text description 164c and a second icon 164d are both used to indicate that the second slider bar is representative of age.

A third slider bar 166a is associated with pathology. In the present embodiment, a third text description 166c and a third icon 166d are both used to indicate that the third slider bar is representative of pathology.

In other embodiments, only text descriptions or only the icons may be used to identify the slider bars.

In use, the user uses the first, second and third slider bars 162a, 164a, 166a to indicate the importance of each similarity dimension (which may also be referred to as each attribute a). In the present embodiment, there are three similarity dimensions: gender, age and pathology. In other embodiments, additional or alternative similarity dimensions may be used. The user interface provides a tool to the user to specify the preferred importance of various attributed in determining similarity.

The slider value represents importance values $f_a$ for each attribute a as values between 0 and 1.

In the embodiment shown in FIG. 9a, the user wishes to obtain a match on gender and pathology. The user has set the importance of gender to a high positive value (0.8) by moving a first slider control 162b along the first slider bar 162a. The user has set the importance of age to a low value, (0.2) by moving a second slider control 164b along the second slider bar 164a. The user has set the importance of pathology to a maximum value (1) by moving a third slider control 166b along the third slider bar 166a.

The slider bars 162a, 164a, 166a provide a filter through which importance of different similarity dimensions (attributes) can be indicated by the user. The user-specified importance of each similarity dimension is reflected in the feature weighting.

Figure 9B:
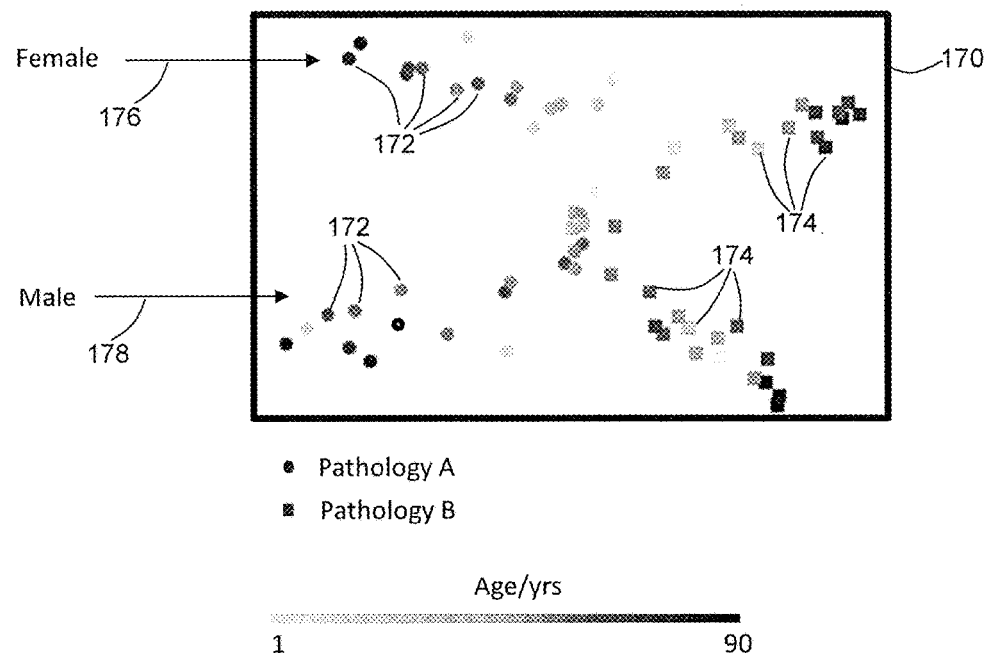

FIG. 9b represents a two-dimensional projection of a multi-dimensional similarity space 170, which may also be referred to as an embedding space. In the present embodiment, the projection of the embedding space 170 is not represented as part of the user interface. However, it is included here to assist the description of the determining of similarity in this embodiment.

Points 172, 174 in the projection of the embedding space are each representative of a respective medical data sets. Points 172 represented by round markers are representative of medical data sets in which a first pathology, Pathology A, is present. Points 174 represented by square markers are representative of medical data sets in which a second pathology, Pathology B, is present. Greyscale values of the points are representative of patient age.

In FIG. 9b, the embedding in similarity space has been performed using the importances indicated by the user in the user interface of 160 of FIG. 9a.

The positions of the points are a 2D projection of the patient cases in the embedding space. The positions of the points in the embedding space are dependent on the importance values that were specified by the user using the user interface.

In the embodiment of FIGS. 9b, points representing female patients are indicated by a first arrow 176 and points representing male patients are indicated by a second arrow 178.

It can be seen in FIG. 9b that points appear to cluster by gender (female at the top of the plot and male at the bottom of the plot) and by pathology (pathology A at the left of the plot and pathology B at the right of the plot), but do not appear to cluster by age. In FIG. 9b, points representing medical data sets having a given gender (or pathology) appear in the same region of the embedding space as other points representing medical data sets with the same gender (or pathology), while appearing in a different region from points representing medical data sets with a different gender (or pathology).

The positioning of the points 172, 174 in similarity space is in accordance with the importances that were indicated by the user using the slider bars 162a, 164a, 166a.

Figure 10A:
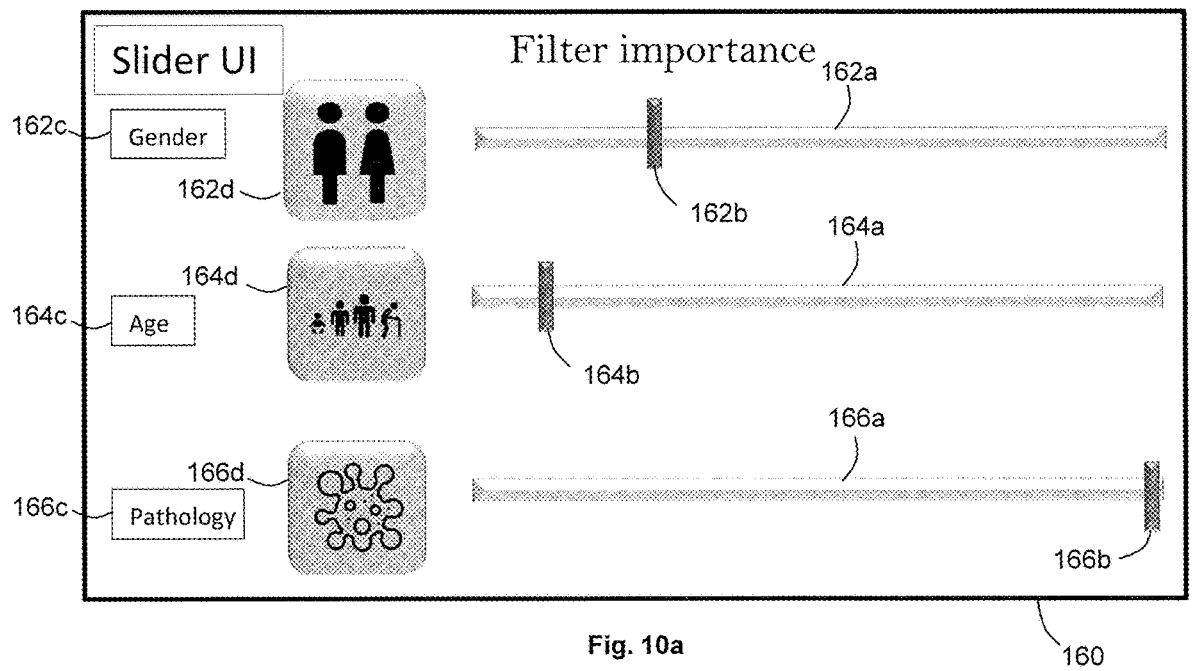
FIG. 10a is a schematic illustration of a user interface in accordance with an embodiment, in which slider bars are used to select importance values.

FIG. 10a is representative of the same user interface as that of FIG. 9a, with the same three sliders 162a, 164a, 166a which are used to select an importance of each of gender, age and pathology. In the embodiment of FIG. 10a, the user wishes to obtain a match on pathology. Gender is given lower importance (0.3) than was the case in FIG. 9b. The importance of gender is indicated by the position of the first slider control 162b on the first slider bar 162a in FIG. 10a. Age is given low importance (0.1), as indicated by the position of the second slider control 164b on the second slider bar 164a in FIG. 10a. Pathology is given maximum importance (1), as indicated by the third slider control 166b on the third slider bar 164a in FIG. 10a.

It may be the case that the same attributes may be less importance in one given clinical scenario than in another clinical scenario, which may motivate the user to input different importance values.

Figure 10B:
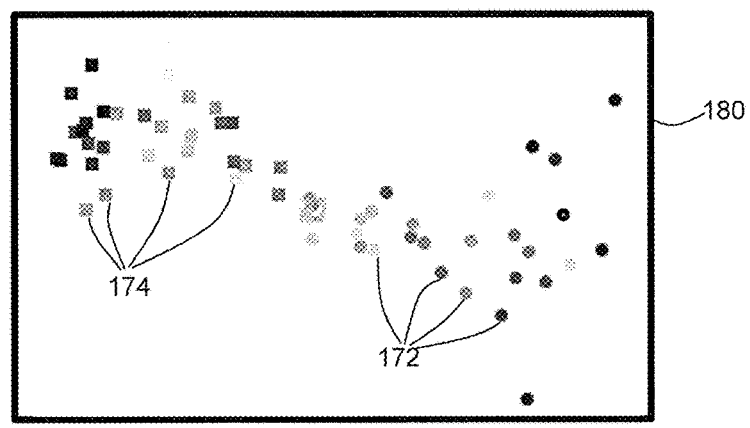
Figure 10B:
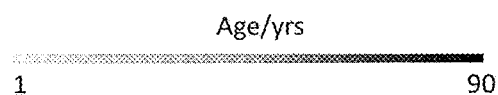

FIG. 10b shows a two-dimensional projection 180 of the embedding space that corresponds to the importance values of FIG. 10a. The embedding space may be considered to be the same embedding space as that of FIG. 9b. Different weights have been applied (due to different attribute importance values being chosen) which warps the space such that the feature axes are now scaled differently. The scaling affects the 2D projection of the feature axes. Points may be brought closer together or further apart depending on their similarity with respect to the newly chosen attribute importance values.

The 2D projection of patient cases in the embedding space is affected by the filter importance as input by the user using the sliders 162a, 164a, 166a.

Points represented by round markers 172 are representative of medical data sets in which a first pathology, Pathology A, is present. Points represented by square markers 174 are representative of medical data sets in which a second pathology, Pathology B, is present. Greyscale values of the points are representative of patient age.

It may be seen that in FIG. 10b, points predominantly appear to cluster by pathology and do not appear to cluster by age or gender. Points representative of medical data sets having pathology B appear to the left of the plot. Points representative of medical data sets having pathology A appear to the right of the plot.

Figure 11A:
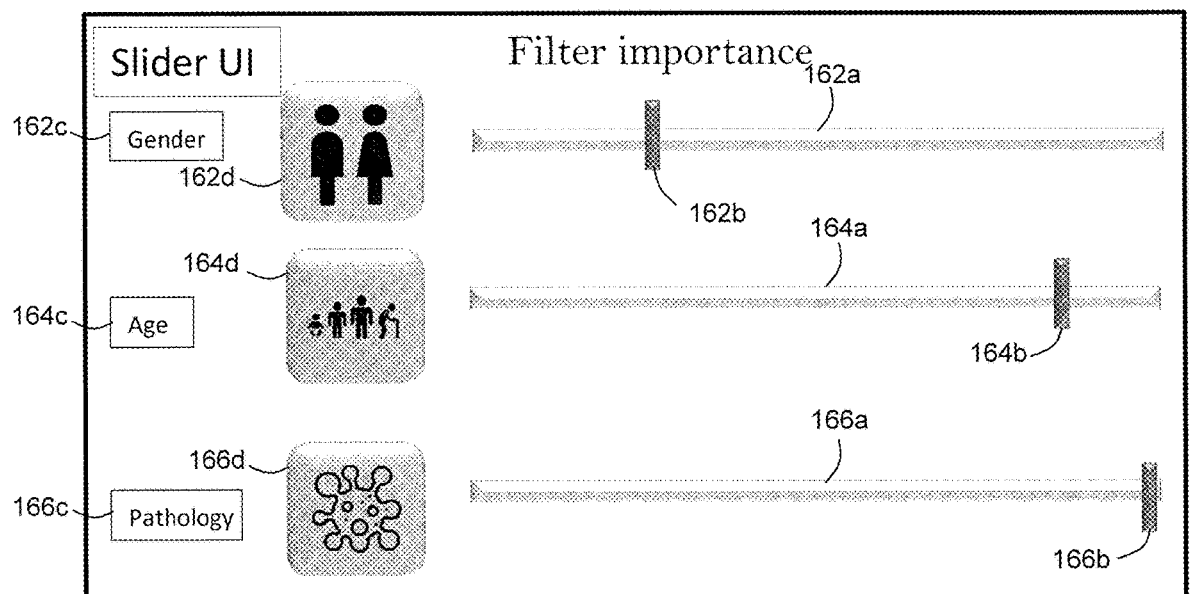
FIG. 11a is a schematic illustration of a user interface in accordance with an embodiment, in which slider bars are used to select importance values.

FIG. 11a is representative of the same user interface as that of FIGS. 9a and 10a, with the same three sliders 162a, 164a, 166a which are used to select an importance of each of gender, age and pathology. In the embodiment of FIG. 11a, the user wishes to obtain a match on age and pathology. Gender is given the same importance (−0.4) as in FIG. 11a. The importance of gender is indicated by the position of the first slider control 162b on the first slider bar 162b in FIG. 11a. Age is given high importance (0.8), as indicated by the position of the second slider control 164b on the second slider bar 164a in FIG. 11a. Pathology is given maximum importance (1), as indicated by the third slider control 166b on the third slider bar 166a in FIG. 11a.

Figure 11B:
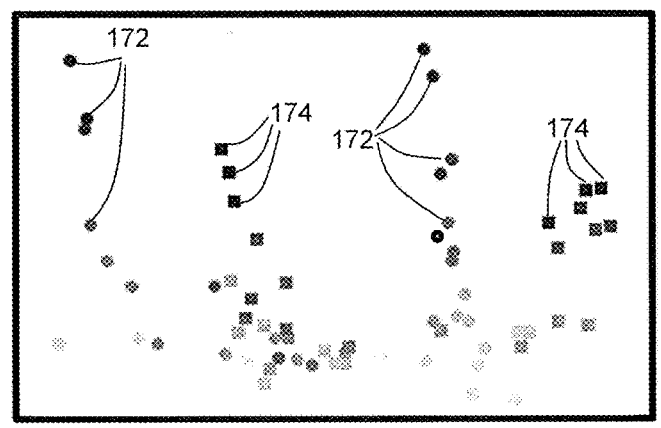

FIG. 11b shows a two-dimensional projection 182 of the embedding space that corresponds to the importance values of FIG. 11a.

Points represented by round markers 172 are representative of medical data sets in which a first pathology, Pathology A, is present. Points represented by square markers 174 are representative of medical data sets in which a second pathology, Pathology B, is present. Greyscale values of the points are representative of patient age.

In FIG. 11b, it may be seen that points appear to cluster by age, with younger ages being towards the bottom of the plot and older ages being towards the top of the plot. Points also appear to cluster by pathology. In the case of FIG. 11b, the points may be considered to form four main groupings, each assuming a different position along a horizontal axis of FIG. 11b. From left to right, the groupings include: a first group of points having pathology A; a second group of points having pathology B; a third group of points having pathology A; and a fourth group of points having pathology B.

In the example shown in FIG. 11b, pathologies A and B are separated as required by the high importance chosen by the user for pathology in FIG. 11a. In this case, pathologies A and B are not unimodal and thus there are different clusters clearly visible in FIG. 11b. The system has learned to identify subtypes of each pathology within the image. It may therefore be seen that weak image-level pathology-level labels may be used to learn rich representations from images.

Figure 12:
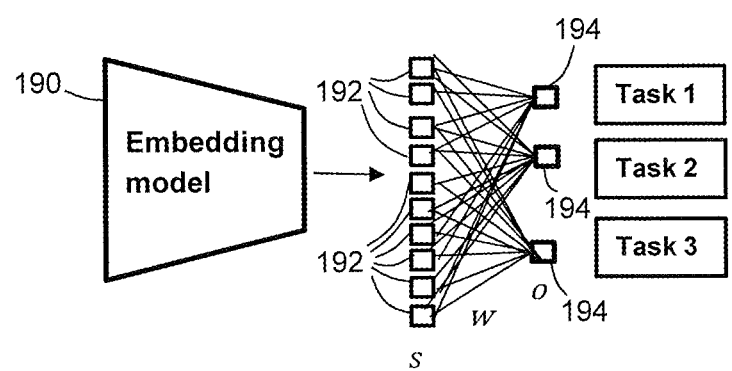
FIG. 12 is a schematic illustration of direct output weighting using an embedding model.

FIG. 12 is a schematic illustration of an alternative embodiments, which may be referred to as direct output weighting. An embedding model 190 is generated using a method as described above with relation to FIG. 3, in which the embedding model is trained on three classification tasks $o_a$. The embedding model outputs a plurality of features 192. The embedding model further outputs a prediction 194 for each of the classification tasks.

In the method described above in relation to FIG. 6, weightings $w_a$ relate the features to the classification tasks. The weightings $w_a$ are combined with importance values $f_a$ for attributes to obtain similarity.

In direct output weighting, the prediction 194 for each task $o_a$ is weighted according to the user preference $f_a$, instead of the individual features 192 being weighted according to the user preference.

$$\text{weighted output} = \sum_{a=1}^{m} f_a \times o_a$$

In direct output weighting as shown, it may be considered that the embedding has only three features. The medical data sets are classified and then the classifications are weighted. The prediction for each attribute is directly weighted by the user's chosen importance weighting. It may be likely that some interesting information about the patients (dimensions of variation) has not been captured at all in this very low dimensional space.

In the embodiment of FIG. 6, weighting features from the fully connected layer may capture both the specified dimension of interest and emergent attributes not explicitly targeted by any of the tasks.

Figure 13:
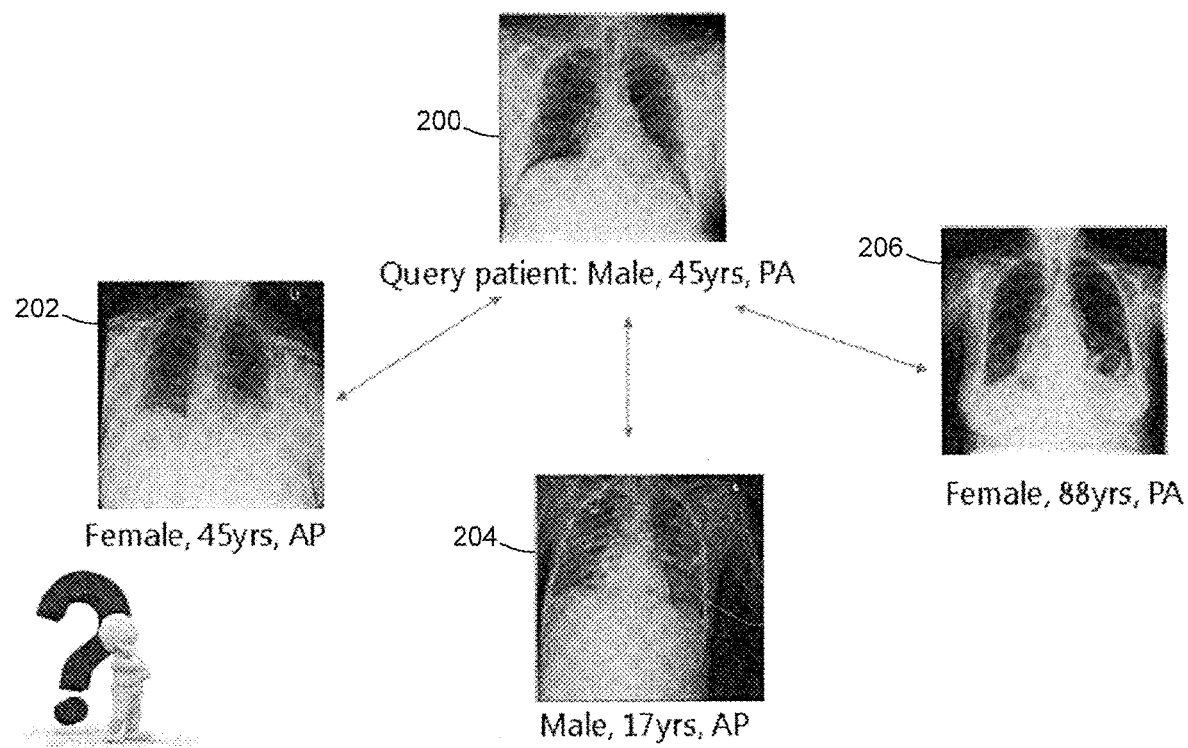
FIG. 13 illustrates an example of a query that may be addressed using the method of FIG. 6.

FIG. 13 illustrates an example of a query that may be addressed using the method of FIG. 6. A image 200 is shown for a query patient. The query patient is male and 45 years old, and the scan view is posterior-anterior (PA). FIG. 13 shows examples 202, 204, 206 of images to which the image for the query patient may be compared. Image 202 is for a patient who is female and 45 years old, and the scan view is anterior-posterior (AP). Image 204 is for a patient who is male and 17 years old, and the scan view is AP. Image 206 is for a patient who is female and 88 years old, and the scan view is PA. One may ask the question of which patient is most similar to the query patient. The answer may depend on which dimension or dimensions of similarity are considered to be of most importance.

Figure 14:
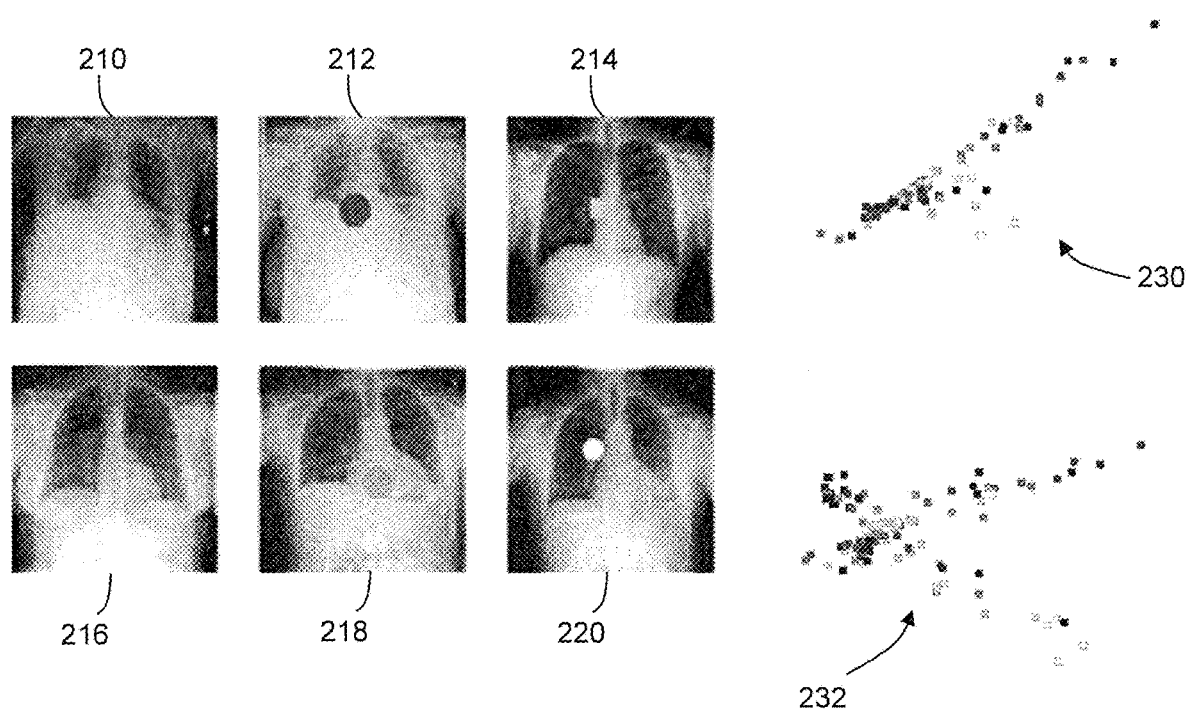
FIG. 14 is a schematic illustration of an example which may be described as a toy problem.

FIG. 14 shows a set of medical images 210, 212, 214, 216, 218, 220 in which simulated pathologies have been inserted. The simulated pathologies are squares and circles having various shades of grey to simulate various severities. FIG. 14 also shows two plots 230, 232. Plot 230 shows a projection of the embedding space in which pathology severity (shades of grey) is considered. Plot 232 shows a projection of the embedding space in which similarity is considered in terms of pathology type (squares and circles).

An exemplary implementation of an embodiment was performed with real data in a first experiment. The data used was obtained from the NIH Chest X-ray 14 data set (Wang X, Peng Y, Lu L, Lu Z, Bagheri M, Summers R M. ChestX-ray8: Hospital-scale Chest X-ray Database and Benchmarks on Weakly-Supervised Classification and Localization of Common Thorax Diseases. IEEE CVPR 2017). This data set contains information about patient age and gender and view position of the scan along with imaging data. Data was removed if the data has an obviously invalid label, for example an age of 404 years old. If there was more than one image per patient, the first scan was selected for training and the other scans were withheld for a further experiment (validation). The whole data set had 30802 patients out of which one image from each of 30000 patients was used for training of the network.

The scans were downsized to 224×224 pixels for efficient training of the network. Each of the attributes (including patient age, gender, view position) was scaled between 0 and 1 before the training.

A training procedure comprising a machine learning process was performed. The training procedure alternated between unsupervised and multi-task training.

Figure 15:
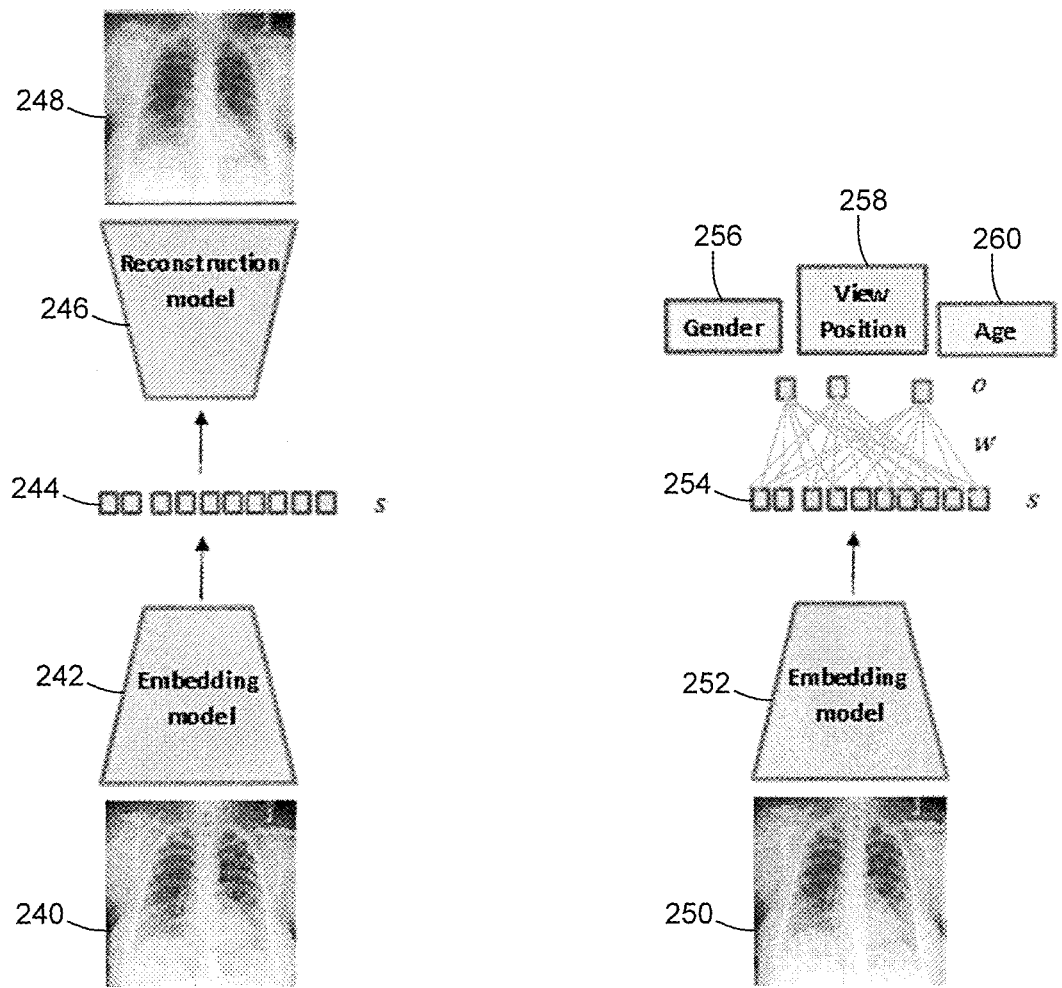
FIG. 15 is a schematic illustration of a training method in accordance with an embodiment.

FIG. 15 illustrates the alternating between reconstruction and multi-task training. Reconstruction is used as a surrogate attribute for similarity based only on appearance. Similarity based on appearance measures how closely matched each pixel is in terms of greyscale value. If no other attributes other than similarity based on appearance are selected, the system should regress to just matching on appearance since the similarity space will be made from these reconstruction features.

Reconstruction is shown on the left of FIG. 15. An embedding model 242 is applied to an image 240 to obtain an embedding vector 244. A reconstruction model 246 is then applied to the embedding vector 244 to obtain a reconstructed image 248.

Multi-task training is shown on the right of FIG. 15. An embedding model 252 is applied to an image 250 to obtain an embedding vector 254. The embedding vector 254 is used to obtain values for gender 256, view position 268, and age 260.

For efficiency reasons in the first experiment, the embedding vectors were first clustered using MiniBatch K-Means into 100 clusters, with mini batch size 100. For each query image, the closest cluster to the query image was found. Cosine similarity was then computed between the embedding of the query image and each image in the closest cluster.

For each test image, the 10 most similar images from the training set were retrieved, with their associated labels.

Certain embodiments provide medical data retrieval of similar cases, method comprising:
  finding a low dimension representation (similarity space) of the clinical case by training a neural network on the classification (or regression) of multiple attributes.
  presenting to the user, those cases which are closest to the current case, according to a distance measure in the low dimensional similarity space.
  providing a tool to the user to specify the preferred importance of various attributes in determining similarity
  said preferred importance is implement by applying weights to the dimensions of the similarity space with respect to each attribute's importance, attribute weights having been determined at training time, from the final layer of the network.

Certain embodiments provide an apparatus for determining similarity between medical data sets for a plurality of patients or other subjects, the apparatus comprising: at least one data store that stores, for a plurality of medical data sets, a respective representation of each of the plurality of medical data sets, the representation of each data set being generated by applying a machine learning process to the plurality of data sets to obtain based on classification and/or regression a model for representing data sets with respect to a plurality of features; and a processing resource that is configured to: use the model obtained by the machine learning process to obtain a representation of a further medical data set; perform a similarity determining process to determine similarity between the representation of a further medical data set and at least some of said representations of said plurality of data sets, wherein each of the representations comprises a set of data elements and for each representation at least some of the data elements have greater importance for determining similarity in respect of some attributes and have lesser importance for determining similarity in respect of some other attributes, and the processing resource is further configured to: select at least one attribute, or select an attribute weighting for at least one of the attributes, for use in the similarity determining process for the further data set; and for at least some of the data set representations, selectively apply different weightings to at least some of data elements of the representation for use in the similarity determining process, depending on attributes or attribute weightings that have been selected, and on the relative importance of the different data elements for the selected attributes or attribute weightings.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus for determining similarity between medical data sets for a plurality of patients or other subjects, the apparatus comprising:
    at least one data store that stores, for a plurality of medical data sets, a respective representation of each of the plurality of medical data sets, the representation of each medical data set being generated by applying a model to the plurality of medical data sets, the model being obtained by applying a machine learning process to a plurality of training data sets to obtain the model based on classification and/or regression, wherein the representation for each medical data set comprises a respective plurality of data elements corresponding to a plurality of features of said medical data set; and
    a processing resource that is configured to:
    use the model obtained by the machine learning process to obtain a representation of a further medical data set;
    select at least one attribute of a plurality of attributes, or select an attribute weighting for at least one of the plurality of attributes, wherein the attributes are representative of dimensions of similarity; and
    perform a similarity determining process to determine similarity between the representation of the further medical data set and at least some of said representations of said plurality of medical data sets, wherein the similarity determining process comprises selectively applying different weightings to at least some of data elements of said representations depending on the at least one attribute or at least one attribute weighting that has been selected, and depending on a relative importance of the different data elements of said representations for the selected attributes or attribute weightings,
    wherein at least some of the data elements of the representations have greater importance for determining similarity in respect of some attributes and have lesser importance for determining similarity in respect of some other attributes.

2. The apparatus according to claim 1, wherein the further data set and/or at least some of the medical data sets comprise image data.

3. The apparatus according to claim 1, wherein the machine learning process comprises generating a succession of layers each layer comprising a set of data elements, and each layer being based upon preceding layer(s), and said representations of the medical data sets correspond to a final layer of the succession of layers generated by the machine learning process.

4. The apparatus according to claim 1, wherein the machine learning process comprises generating a succession of layers each layer comprising a set of data elements, and each layer being based upon preceding layer(s), and said representations of the medical data sets correspond to a layer that can be used to determine similarity both with respect to said plurality of features and with respect to emergent features not explicitly included in said plurality of features.

5. The apparatus according to claim 1, wherein the processing resource is configured to perform the selective applying of different weightings without altering the machine learning process and/or without altering inputs to the machine learning process.

6. The apparatus according to claim 1, wherein the selective applying of different weightings comprises applying both negative and positive weightings.

7. The apparatus according to claim 1, wherein the machine learning process comprises at least one of a convolutional neural network (CNN) process, a classifier training process, the performance of similarity determination tasks with respect to said plurality of features.

8. The apparatus according to claim 1, wherein the processing resource is further configured to select at least one of the medical data sets based on similarity to said further medical data set determined using the similarity determining process, and outputting at least part of the selected medical data set or outputting an identifier that identifies the selected medical data set.

9. The apparatus according to claim 8, wherein at least some of the medical data sets comprise at least some medical imaging data, the apparatus further comprises a display and the outputting at least part of the selected medical data set comprises displaying on the display an image represented by the medical imaging data.

10. The apparatus according to claim 1, further comprising a user interface configured to receive user input, wherein the selecting at least one of the attributes, or selecting an attribute weighting is based on the user input.

11. The apparatus according to claim 10, wherein the user interface comprises at least one of a slider, button, list of values, list of attributes, at least one selectable element.

12. The apparatus according to claim 1, wherein selecting at least one of the attributes, or selecting the attribute weighting, for use in the similarity determining process is based on at least one of: a clinical scenario relevant to the further data set; a type of image data included in the further data set; an imaging modality; results of at least one further test or procedure performed on the patient or other subject of the further data set.

13. The apparatus according to claim 1, wherein at least one of a) or b):
    a) the attributes comprises at least one image attribute and at least one non-image attribute;

b) the representations of the data sets comprise representations that are compressed and/or of reduced dimension in comparison to the data sets.

14. The apparatus according to claim 1, wherein the attributes comprise at least one of age; gender; presence, absence or nature of pathology; presence or absence of anatomical feature; at least one parameter of anatomical feature; ethnicity; coexisting condition; point in treatment pathway; time since onset; treatment applied; time since treatment.

15. The apparatus according to claim 1, wherein the further data set and/or at least some of the medical data sets comprise data representing at least one property of the patient or other subject of the data set in question.

16. The apparatus according to claim 1, wherein the further data set and/or at least some of the medical data sets comprise image data obtained by a scan performed on the patient or other subject of the data set in question.

17. The apparatus according to claim 16, wherein the image data comprises at least one of CT data, MRI data, X-ray data, fluoroscopy data, PET data, ultrasound data.

18. A method of determining similarity between medical data sets for a plurality of patients or other subjects, the method comprising:
storing for a plurality of medical data sets a respective representation of each of the plurality of medical data sets, the representation of each data set being generated by applying a model to the plurality of medical data sets, the model being obtained by applying a machine learning process to a plurality of training data sets to obtain the model based on classification and/or regression, wherein the representation for each medical data set comprises a respective plurality of data elements corresponding to a plurality of features of said medical data set;
using the model obtained by the machine learning process to obtain a representation of a further medical data set;
selecting at least one attribute of a plurality of attributes, or selecting an attribute weighting for at least one of the plurality of attributes, wherein the attributes are representative of dimensions of similarity; and
performing a similarity determining process to determine similarity between the representation of the further medical data set and at least some of said representations of said plurality of medical data sets, wherein the similarity determining process comprises selectively applying different weightings to at least some of data elements of said representations depending on the at least one attribute or at least one attribute weighting that has been selected, and depending on a relative importance of the different data elements of said representations for the selected attributes or attribute weightings,
wherein at least some of the data elements of the representations have greater importance for determining similarity in respect of some attributes and have lesser importance for determining similarity in respect of some other attributes.

19. A non-transitory computer program product comprising computer-readable instructions that are executable to:
store for a plurality of medical data sets a respective representation of each of the plurality of medical data sets, the representation of each data set being generated by applying a model to the plurality of medical data sets, the model being obtained by applying a machine learning process to a plurality of training data sets to obtain the model based on classification, wherein the representation for each medical data set comprises a respective plurality of data elements corresponding to a plurality of features of said medical data set;
use the model obtained by the machine learning process to obtain a representation of a further medical data set;
select at least one attribute of a plurality of attributes, or select an attribute weighting for at least one of the plurality of attributes, wherein the attributes are representative of dimensions of similarity; and
perform a similarity determining process to determine similarity between the representation of the further medical data set and at least some of said representations of said plurality of medical data sets, wherein the similarity determining process comprises selectively applying different weightings to at least some of data elements of said representations depending on the at least one attribute or at least one attribute weighting that has been selected, and depending on a relative importance of the different data elements of said representations for the selected attributes or attribute weightings,
wherein at least some of the data elements of the representations have greater importance for determining similarity in respect of some attributes and have lesser importance for determining similarity in respect of some other attributes.

* * * * *